(12) United States Patent
Nelson et al.

(10) Patent No.: US 6,682,504 B2
(45) Date of Patent: Jan. 27, 2004

(54) SINGLE USE DISPOSABLE JET INJECTOR (75) Inventors: Sheldon J. Nelson, Plymouth, MN (US); Kenneth L. Adam, Chanhassen, MN (US); Claude L. Berman, Ypsilanti, MI (US); Peter L. Sadowski, Woodbury, MN (US); Paul R. Lesch, Jr., Lexington, MN (US)

(73) Assignee: Antares Pharma, Inc., Minneapolis, MN (US)

( * ) Notice: Subject to any disclaimer, the term of this patent is extended or adjusted under 35 U.S.C. 154(b) by 309 days.

(21) Appl. No.: 09/813,889

(22) Filed: Mar. 22, 2001

(65) Prior Publication Data
US 2002/0007149 A1 Jan. 17, 2002

Related U.S. Application Data
(60) Provisional application No. 60/191,469, filed on Mar. 23, 2000.

(51) Int. Cl.⁷ .................................................. A61M 5/30
(52) U.S. Cl. .......................................... 604/70; 604/141
(58) Field of Search ............................... 604/68–70, 72, 604/82, 86–91, 110, 181, 186–187, 200–201, 203, 205, 218, 220, 221, 141, 140, 134–135, 137–139; 128/919

(56) References Cited

U.S. PATENT DOCUMENTS

| | | | | |
|---|---|---|---|---|
| 2,547,099 A | * | 4/1951 | Smoot | 604/70 |
| 3,115,133 A | * | 12/1963 | Morando | 604/70 |
| 3,948,266 A | * | 4/1976 | Clark et al. | 604/72 |
| 5,391,151 A | * | 2/1995 | Wilmot | 604/139 |
| 5,599,302 A | * | 2/1997 | Lilley et al. | 604/68 |
| 5,954,689 A | * | 9/1999 | Poulsen | 604/71 |
| 6,132,395 A | * | 10/2000 | Landau et al. | 604/68 |
| 6,391,003 B1 | * | 5/2002 | Lesch, Jr. | 604/110 |

* cited by examiner

Primary Examiner—LoAn H. Thanh
(74) Attorney, Agent, or Firm—Winston & Strawn LLP (57) ABSTRACT

A jet injector having cartridge and power pack assemblies is disclosed. In one embodiment, the cartridge assembly includes a tube containing the medicament with a plunger at one end and a stopper at the other end. The plunger is movable within the tube lumen to force the stopper against a needle, thereby creating a fluid pathway through the stopper. In another embodiment, only the plunger is movable within the tube lumen and the stopper, which can be integral to the rest of the cartridge assembly or a separate component, already has a pathway for ejection of the medicament. The present invention also relates to an energy mechanism for the power pack assembly that is a gas spring containing a charging material existing in liquid and gaseous phase equilibrium within the gas spring to maintain a substantially constant pressure prior to activation.

32 Claims, 5 Drawing Sheets

SINGLE USE DISPOSABLE JET INJECTOR

CROSS-REFERENCE TO RELATED APPLICATIONS

The benefit of Provisional Application No. 60/191,469 filed on Mar. 23, 2000 is claimed under 35 U.S.C. § 119(e).

FIELD OF THE INVENTION

The present invention is directed to a device for delivery of medicament, and in particular to a single use disposable jet injector.

BACKGROUND OF THE INVENTION

A wide variety of needle free injectors are known in the art. Examples of such injectors include those described in U.S. Pat. No. 5,599,302 issued to Lilley et al., U.S. Pat. No. 5,062,830 to Dunlap, and U.S. Pat. No. 4,790,824 to Morrow et al. In general, these and similar injectors administer medication as a fine, high velocity jet delivered under sufficient pressure to enable the jet to pass through the skin.

Although these injectors are quite successful from a technical point-of-view in achieving the desired delivery of medicament, most commercially available needle free injectors have practical limitations. For example, the use of a gas to power the jet injection, in the form of a gas spring or otherwise, has been problematic because of the potential for gas leakage with injector storage time and temperature sensitivity of the gas pressure. U.S. Pat. No. 4,913,699 discloses a gas powered disposable injector that uses carbon dioxide ($CO_2$) and depends on the $CO_2$ boiling off in a chamber and pressurizing a chamber that causes the plunger to move. U.S. Pat. No. 4,646,884 discloses an extended life gas spring that compensates for inherent leakage by being charged with gas and liquid such that as the gas leaks out, the liquid is converted to the gas phase. This is a reciprocal gas spring and the usage anticipates a gas spring in continuous service and is not a disposable device.

Another limitation of the prior art is the inability to use some needle free injectors with standard medicament cartridges, i.e. a cylindrical chamber, typically made of glass, having a first end with a seal penetrable by a needle to draw medicament out of the cartridge and a second end with a movable stopper. U.S. Pat. No. 5,891,086 discloses a needle-less injector in which one embodiment works with a sealed cartridge. As the nozzle is placed on one end of the cartridge, a piercing tube breaks the seal. As a result, the medicament in the cartridge is exposed to the nozzle until the injection is made. U.S. Pat. No. 6,132,395 does disclose a needle free injector that can be used with a glass cartridge. However, like the '086 patent, the medicament is exposed to the environment prior to initiation of the injection, thereby potentially compromising the sterility of the medicament.

Thus, a need exists for an improved single use disposable jet injector.

SUMMARY OF THE INVENTION

The present invention relates to a jet injector comprising a cartridge assembly for holding medicament and a power pack assembly for providing energy to eject the medicament from the cartridge assembly with sufficient pressure for jet injection. The cartridge assembly includes a chamber (or tube with a lumen) for holding the medicament therein, an orifice at the proximal end of the cartridge assembly, a stopper at the proximal end of the chamber, and a plunger at the distal end of the chamber and movable toward the stopper to expel medicament out of the chamber through the orifice. The power pack assembly includes a housing having a proximal end operatively coupled with the distal end of the cartridge assembly, a trigger, and an energy source operatively associated with the trigger so that movement of the trigger activates the energy source to move the plunger toward the stopper to expel medicament from the chamber.

In an exemplary embodiment, the energy source is a gas spring containing a charging material existing in liquid and gaseous phase equilibrium within the gas spring to maintain a substantially constant pressure prior to activation. An example of a suitable charging material is carbon dioxide. The gas spring can have a wall with a coating to reduce gas permeability. Additionally, the injector can include a safety vent for releasing excess pressure and/or a temperature indicator for indicating that the jet injector has been exposed to temperatures outside of a set range.

In one embodiment, the cartridge assembly comprises an outer housing made of a polymer and an inner housing made of a glass. At least a portion of the plunger and stopper can be made of an elastomeric material. A needle, which can be beveled, is operatively associated with the proximal end of the cartridge assembly and has a piercing end extending toward the chamber. The stopper is movable within the chamber toward the piercing end of the needle and relative movement between the stopper and the needle causes the piercing end of the needle to pierce the stopper to create a fluid pathway for the medicament through the needle. Movement of the plunger toward the proximal end of the chamber compresses the medicament held between the plunger and the stopper so that the medicament is expelled through the fluid pathway. The movement of the plunger toward the proximal end of the chamber also compresses the medicament between the stopper and the plunger to move the stopper toward the proximal end of the cartridge assembly to allow the piercing end of the needle to pierce the stopper and create the fluid pathway for the medicament through the needle.

The stopper can have a frustroconical shape and the plunger can have a medicament contacting surface configured and dimensioned to mate with the frustroconical shape of the stopper to minimize volume of medicament remaining in the chamber after the injection is completed. In order to facilitate creation of the fluid pathway, the stopper can have a narrow cross-section where the needle penetrates the stopper. In other embodiments, the plunger comprises a front member having a recess and an substantially non-compressible insert received in the recess. Additionally, the plunger and/or stopper can include ridges formed around an outer periphery to provide a seal and create a sterile boundary between the medicament and an exterior of the cartridge assembly.

The power pack assembly can include a distal housing having a lumen containing the charging material and a proximal housing connectable with the distal housing and having an inner surface with a ledge for receiving locking tabs on the cartridge assembly to couple the cartridge assembly thereto. A portion of an exterior surface of the proximal housing has threads and a portion of a lumen wall has threads. The proximal housing threads mate with the lumen wall threads to connect the proximal and distal housings.

In an exemplary embodiment, a ram has a proximal end contacting the plunger and a distal end having a seal so that the gas spring is defined by the lumen wall and the seal. The ram has a recess and the inner surface of the proximal housing has a latch member insertable into the recess to thereby prevent the gas spring from moving the ram and the plunger toward the stopper. Movement of the trigger allows the latch member to bend away from the recess to thereby allow the gas spring to move the ram and the plunger toward the stopper. The trigger can include a tubular body substantially covering the cartridge assembly, a cap operatively associated with the proximal housing, and struts connecting the body and the cap.

DESCRIPTION OF THE PREFERRED EMBODIMENTS

Figure 1:
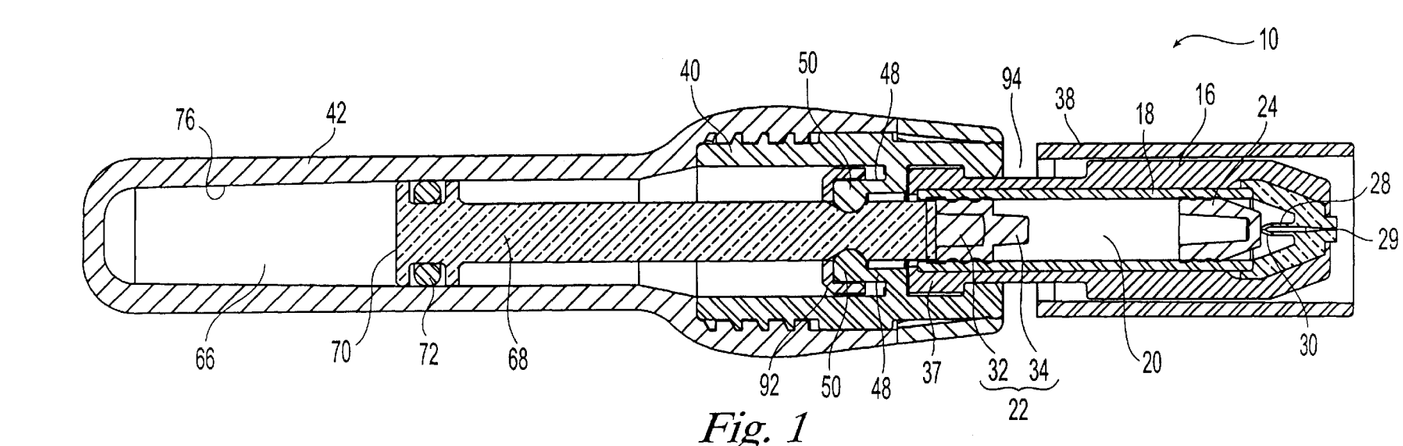
FIG. 1 shows a cross sectional view of one embodiment of the jet injector according to the present invention prior to firing.
Figure 2:
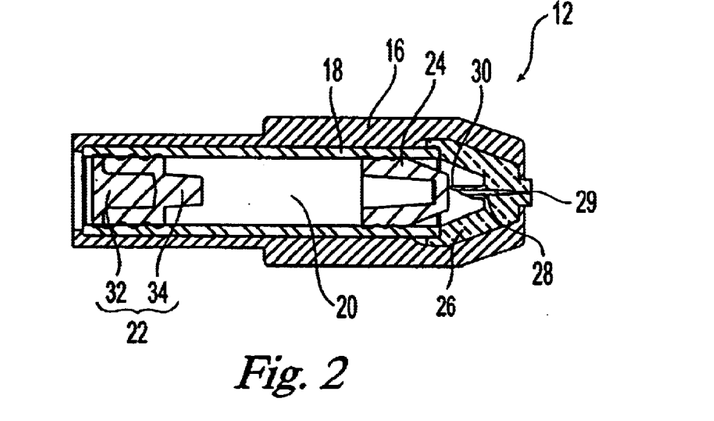
FIG. 2 shows a cross sectional view of one embodiment of a cartridge assembly.

As shown in FIGS. 1 and 2, a jet injector 10 according to the present invention comprises a cartridge assembly 12 containing the medicament to be injected and a power pack assembly 14 for generating sufficient energy to expel the medicament out of cartridge assembly 14 with enough force to be jet injected through the skin. As used herein, the terms proximal and distal are with respect to the injection site so that the power pack assembly 14 located near the distal end is the end of injector 10 farthest from the injection site and the cartridge assembly 12 located near the proximal end of injector 10 is nearest to the injection site. Cartridge assembly 12 can be made of a polymer that possesses both the strength to withstand the pressures associated with jet injection and physical and chemical compatibility with the medicament in cartridge assembly. Examples of suitable polymers include cyclic olefin polymer (COP) and cyclic olefin copolymer (COC). Both COP and COC have barrier properties that allow for long term storage of the medicament within cartridge assembly 12. When a plastic is used that is not suitable for long term drug storage because of its barrier properties, the entirety of injector 10 can be sealed in a pouch with the necessary barrier properties. Since pouching materials with suitable barrier properties may be expensive, it is possible that several injectors are packaged within one pouch, with the injectors to be then used over a discrete period of therapy.

FIG. 2 shows one embodiment of cartridge assembly 12 utilizing an outer housing 16 made of a polymer and an inner housing 18 made of glass. Inner housing 18 is in intimate contact with outer housing 16. For example, inner housing 18 can be formed by coating the inner surface of outer housing 16 with glass. Alternatively, outer housing 18 can be molded over inner housing 18. The plastic-glass combination allows the use of plastics that have the necessary strength properties to withstand the high pressure of jet injection, but may not possess some of the barrier properties necessary for long term drug storage. Such barrier properties are not necessary because glasses such as borosilicate glass and other examples well known to those of ordinary skill in the art have excellent barrier properties and are highly compatible with most medicaments.

In the embodiment of FIG. 2, cartridge assembly 12 comprises a chamber 20 with a plunger 22 (FIGS. 3 and 4) at the distal end and a stopper 24 (FIG. 5) at the proximal end. Chamber 20 defines a volume that has a substantially cylindrical shape and a longitudinal axis. When cartridge assembly 12 is filled with medicament, the surface of chamber 20 and a surface of plunger 22 and stopper 24 will be in contact with the medicament. Because the glass does not define either end of cartridge assembly 12, the medicament chamber also serves as the final drug container. Due to the intimate prolonged contact between the chamber walls and the drug, the advantage of glass as a component of the drug storage container is that a large body of knowledge exists establishing that glass can serve as a suitable container.

Figure 3:
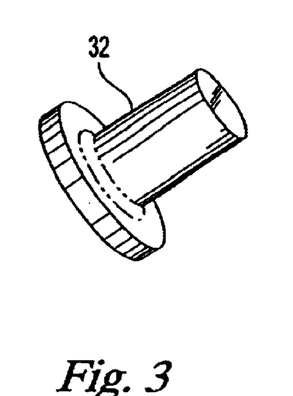
FIG. 3 shows a perspective view of an insert member that can be used to form a two part plunger.
Figure 4:
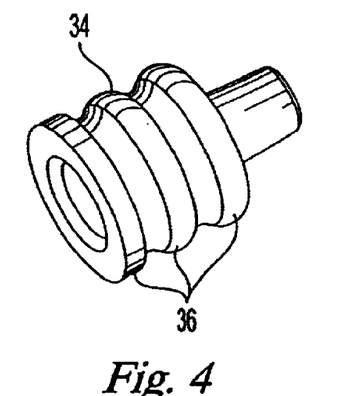
FIG. 4 shows a perspective view of a front member that can be used to form a two art plunger.
Figure 5:
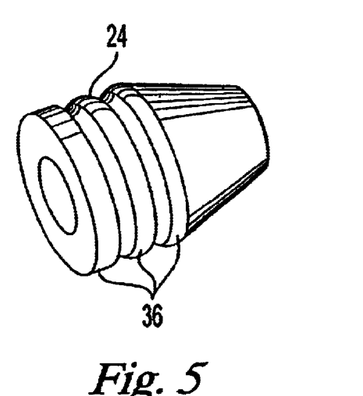
FIG. 5 shows a perspective view of a stopper.

In an exemplary embodiment, plunger 22 and stopper 24 are made of elastomeric pieces. Silicone and similar elastomeric compositions are examples of suitable materials. The incorporation of elastomeric stoppers and plungers allows the use of sealing elements known to the pharmaceutical industry and for which drug chemical compatibility data may exist. Since such compounds are now used in final container drug storage applications, the use of such material to define the ends of the container also draws on a large body of knowledge defining suitable compositions or formulations. Possibly more important or significant is the fact that pharmaceutical manufacturers may already have knowledge about drug stability in glass containers with a given surface area and with elastomeric closures. Such information could then be applicable to the use of the jet injector according to the present invention. Additionally, the use of a compressible stopper to serve as a closure as well as a plunger is intended to facilitate the aseptic filling of these containers by means that are standard to the industry.

Inner housing 18 with elastomeric closures 22, 24 is a stand alone item that could be filled with drug without incorporation into the structure that defines cartridge assembly 12. This feature has several advantages over existing technology or art in this field. Since the drug container defined as including all materials in long term contact with the drug material consists of a glass tube with a lumen and stoppers at either end, this can be tested for drug stability without consideration or involving other components of the device. This allows testing that requires lengthy periods of time to be undertaken without defining the final device configuration and also allows modification to power settings or external features influencing injection quality while the drug stability testing is ongoing. The self contained nature of this final drug storage container allows it to be used in other injection systems that are not needle-free, including but not being limited to a mini-needle device.

As shown in FIG. 2, a needle 28 is operatively associated with the proximal end of cartridge assembly 12. Needle 28 can be formed as a spike protruding from a shield 26. Outer housing 16 couples shield 26 to inner housing 18. Needle 28 terminates in an orifice 29 of a suitable diameter that would produce a jet stream of medicament under a given desired pressure range and depth of injection. Needle 28 has a piercing end 30 that extends toward chamber 20 and, in an exemplary embodiment, can be beveled. In an exemplary embodiment, stopper 24 has a cavity shown as a frustroconical shape and narrow cross-section in the proximal portion for ease of penetration and plunger 22 is configured and dimensioned to mate with the frustroconical shape of stopper 24 to minimize the volume of the medicament remaining in chamber 20 after the injection is completed.

In use and as described in more detail below, the injection firing process applies a force to plunger 22 (via the associated ram) urging plunger 22 in the direction of the proximal end of chamber 20. The movement of plunger 22 in the direction of the proximal end causes compression of the medicament. As the medicament is incompressible to at least some degree, the compression of the medicament results in a force building up on stopper 24. This force continues to build until stopper 24 begins to move. At that time, plunger 22, stopper 24 and the medicament, located in chamber 20, move towards the proximal end of cartridge assembly 12. This array of plunger 22, medicament, and stopper 24 moves as one unit until stopper 24 comes in contact with piercing end 30 of needle 28. Piercing end 30 of needle 28 pierces stopper 24 to create a fluid pathway for the medicament. Stopper 24 ceases to move while plunger 22 continues to respond to the force exerted on it and moves toward the proximal end of tube 20 until all the medicament located in chamber 20 is expelled. Since needle 28 is not introduced to the medicament located in chamber 20 until the latter end of the firing process, any insoluble or particulate constituents in the medicament that may be present cannot settle on needle 28 thereby eliminating any possibilities of needle 28 becoming clogged before firing. The lack of contact between the medicament and needle 28 until just prior to ejection of the medicament through needle 28 also helps to maintain sterility of the medicament until initiation of the injection. Furthermore, there is no need to agitate cartridge assembly 12 to try to mix or re-suspend the particulate matter because it does not contact the needle until the injection device is fired.

FIGS. 3 and 4 show one embodiment in which plunger 22 comprises a two part assembly of insert 32 and front member 34. Front member 34 receives substantially non-compressible insert 32 after placement during the aseptic filling operation thereby significantly decreasing the compressibility of plunger 22. This anticipates the need to minimize the compressibility of plunger 22 during the injection so that effective transmission of force to the medicament in chamber 20 can occur. This also improves the sealing ability of the compressible elastomer at the pressures that are necessary for jet injection. Insert 32 can be integral with the ram as an alternative to a two piece plunger 22. As also shown in FIGS. 3–5, plunger 22 and/or stopper 24 can include a series of ridges 36 formed around its outer periphery to provide a seal and create a sterile boundary between the medicament and the outside of cartridge assembly 12.

Figure 6:
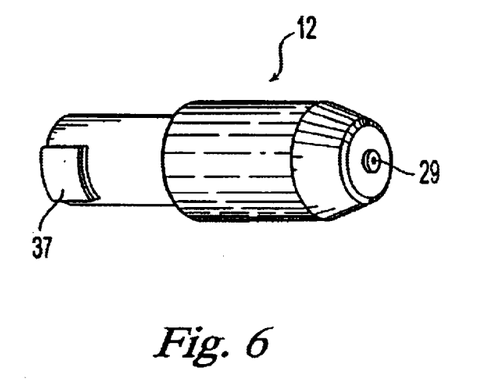
FIG. 6 shows a first perspective view of the cartridge assembly of FIG. 2.
Figure 7:
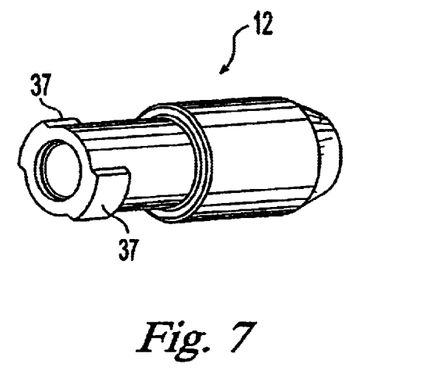
FIG. 7 shows a second perspective view of the cartridge assembly of FIG. 2.

As best seen in FIGS. 6 and 7, the distal end of cartridge assembly 12 has locking tabs 37. Locking tabs 37 mate with corresponding features on power pack assembly 14 to lock cartridge assembly 12 to power pack assembly 14. These and other structural features of power pack assembly 14 will now be described.

Figure 8:
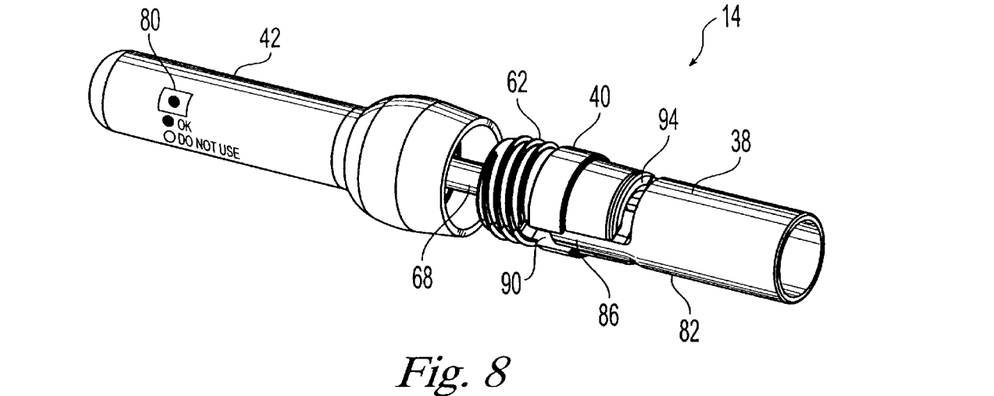
FIG. 8 shows a perspective view of a power pack assembly prior to coupling of the proximal and distal housings.
Figure 9:
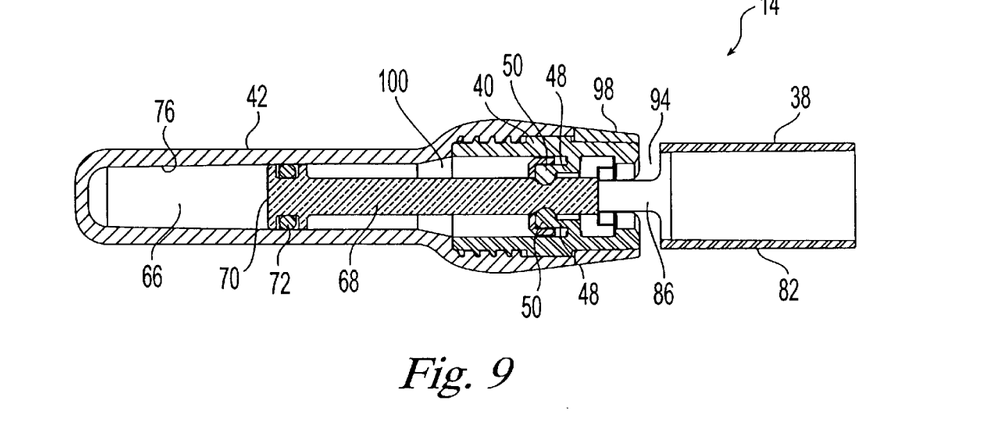
FIG. 9 shows a cross sectional view of the power pack assembly of FIG. 8.
Figure 10:
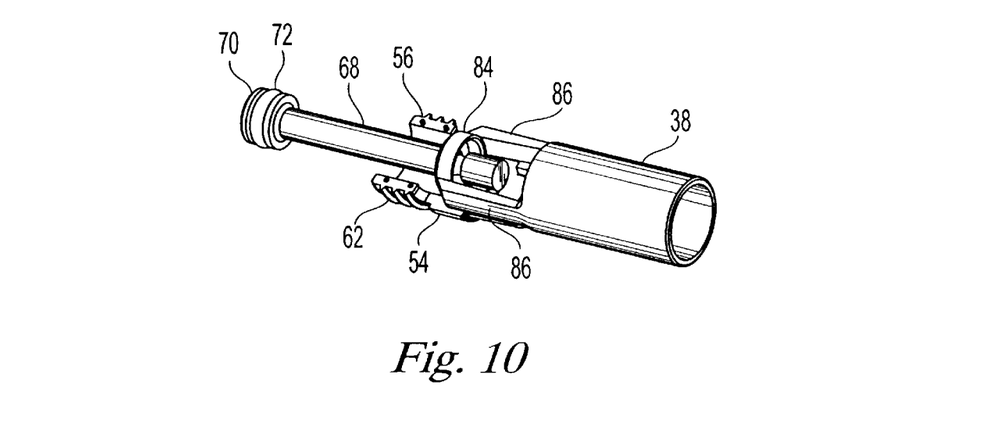
FIG. 10 shows a perspective view of a section of the proximal housing and the collar.
Figure 12:
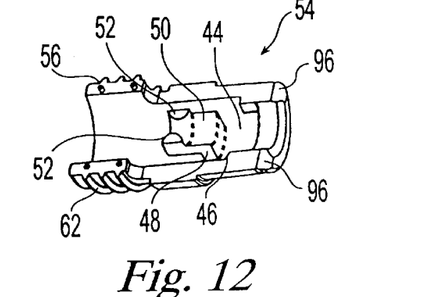
FIG. 12 shows a perspective view of a first section of the proximal housing.
Figure 13:
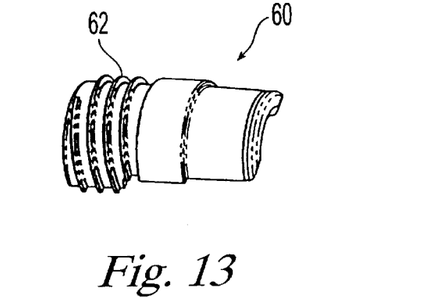
FIG. 13 shows a perspective view of a second section of the proximal housing.

FIGS. 8–10 show that power pack assembly 14 comprises a collar 38 that functions as a trigger and a two part housing that includes a proximal housing 40 and a distal housing 42. The interior of proximal housing 40 is a tube having a lumen (FIGS. 12 and 13). A portion of the lumen has a keyed surface 44 configured and dimensioned to receive the distal end of cartridge assembly 12. Keyed surface 44 terminates in a ledge 46. In order to couple cartridge assembly 12 into proximal housing 40, cartridge assembly 12 is inserted into proximal housing 40 and snapped into place so that locking tabs 37 are located between ledge 46 and a pair of base members 48. A latch 50 extends from each base 48 and has opposed arcuate edges 52 defining a space therebetween. In order to facilitate assembly of power pack assembly 14, proximal housing 40 can be made in two halves. First section 54 has pins 56 that engage holes (not shown) in second section 60 to form proximal housing 40. A portion of the outer surface of proximal housing 40 is provided with threads 62 and a portion of the inner surface of distal housing 42 is provided with threads 64 so that when proximal housing 40 is inserted in distal housing 42, threads 62 mate with threads 64.

Distal housing 42 defines a volume for receiving a ram 68 and for containing an energy mechanism 66 for driving ram 68 toward cartridge assembly 12 with sufficient force to initiate a jet injection. In the shown exemplary embodiment, the energy mechanism comprises a gas spring 66 containing a gas, such as carbon dioxide, located in the volume between the distal end of distal housing 42 and a distal end 70 of ram 68. Other gases and energy mechanisms capable of generating sufficient force for jet injection are also contemplated by the present invention. Examples of such energy mechanisms include coil springs and gas cartridges.

A sealing member, such as o-ring 72 located in groove 74, provides a seal to reduce loss of gas. In order to ensure that the gas spring has sufficient pressure to jet inject the medicament even if injector 10 has been stored for an extended period of time, the gas spring can contain carbon dioxide in both gas and liquid or saturated vapor phases. The gas and liquid or saturated vapor are in equilibrium. As a result, as gas leaks with time, the vapor changes into gas to maintain adequate pressure for jet injection. A wall 76 of gas spring 66 can be made of a material that has a low permeability to the gas. Examples of such materials include long glass fiber filled nylon and long glass fiber filled nylon with clay nano-composite. Additionally, wall 76 can include a coating, such as parylene, to minimize the permeability of gas spring 66 and thereby reduce gas leakage.

Figure 11:
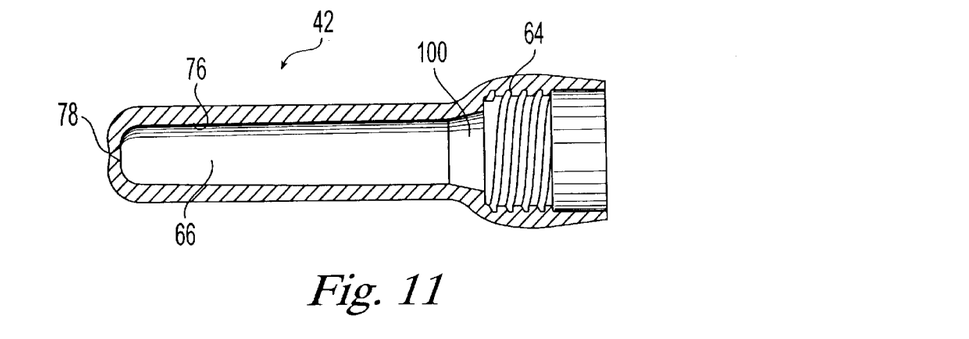
FIG. 11 shows a cross sectional view of one embodiment of the distal housing.

Since the amount of pressure in the gas spring is dependent on the temperature of the gas, a mechanism can be incorporated into the gas spring that results in the de-pressurization of the gas spring when the spring pressure exceeds some predetermined value. FIG. 11 shows one embodiment of this mechanism. Specifically, a safety vent 78 is located on distal housing 42. Safety vent 78 vents to release excess gas when the pressure exceeds a given pressure, such as 2000 p.s.i. This assures that injector 10 is not used when the force of the gas spring would be too high and also allows for the release of excessive pressures that may cause uncontrolled material failures of the various components of injector 10.

FIG. 8 shows another mechanism that can be used to verify a desired pressure in the gas spring. A temperature indicator 80 indicates to the user that the force to be generated by the gas spring is optimal. In one embodiment, temperature indicator 80 is a chemical sensor affixed to distal housing 42 with the chemistry set so as to give an indication that injector 10 is alright to use. The use of a color such as green to indicate that the device is at a temperature allowing use, and alternatively red when the device is too cold or hot to be used. These could be symbols or any other indicators that are readily interpreted. The described chemical sensor is a passive indicator that may not render injector 10 inoperable. However, incorporating an active indicator that renders injector 10 inoperable is also contemplated by this invention. It is also contemplated that the temperature range at which the chemical sensor indicates an acceptable temperature could be drug dependent. For example, some medicaments could become inactive at temperatures below 50° F. and above 120° F., while other medicaments could have a larger range of suitable temperatures before significant degradation.

Figure 14:
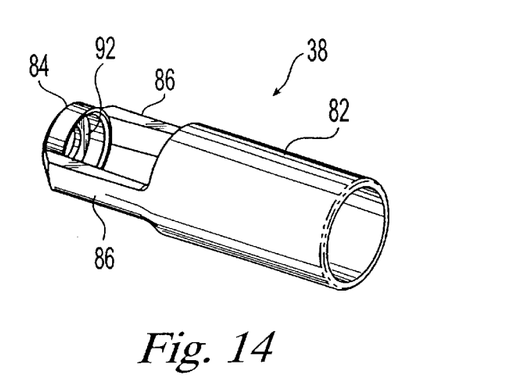
FIG. 14 shows a perspective view of a collar that can be used to trigger firing.
Figure 15:
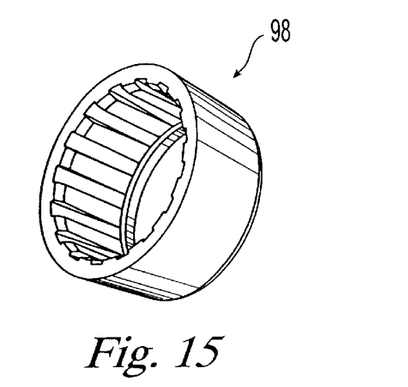
FIG. 15 shows a perspective view of a housing retainer for maintaining the coupling of the cartridge assembly and the power pack assembly.
Figure 16:
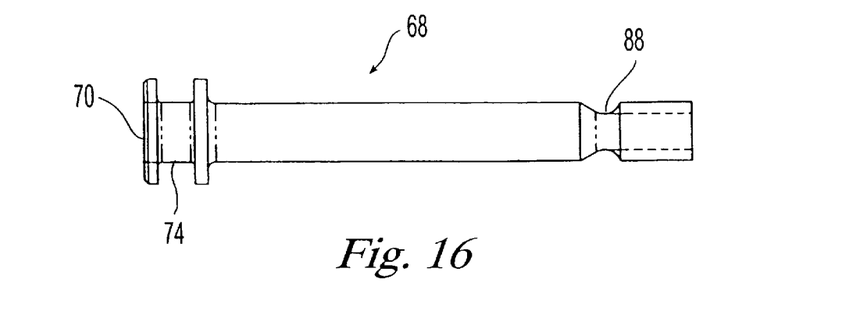
FIG. 16 shows a side view of a ram.

Although there are a number of different ways to assemble power pack assembly 14, an exemplary method will now be described. A proximal portion of ram 68 is placed into collar 38. As best seen in FIG. 14, collar 38 comprises a tubular body 82, a cap 84, and struts 86 connecting body 82 to cap 84. Ram 68 is then placed into first section 54 of proximal housing 40 so that a recess 88 lies within the space defined by opposed edges 52 on latch 50. Second section 60 is then mated with first section 54 to form proximal housing 40. When so mated, a channel 90 (FIG. 8) exists along a portion of proximal housing 40. Struts 86 can slide within channel 90. When proximal housing 40 has been assembled, collar 38 is slid in the proximal direction so that a rim 92 on cap 84 clips between latch 50 and the wall of proximal housing 40 (FIG. 9). As is evident from FIG. 8, a gap 94 is located between body 82 of collar 38 and proximal housing 40 when the sub-assembly of ram 68, collar 38, and proximal housing 40 is completed. It should be noted that some type of blocking member could be placed in gap 94 to provide a safety mechanism that prevents unintentional movement of the collar 38.

Prior to coupling proximal housing 40 to distal housing 42, solid $CO_2$ is placed into gas spring 66. The amount of $CO_2$ is sufficient such that there would be an equilibrium of gas and saturated liquid $CO_2$ present in the sealed chamber. As previously noted, this saturated liquid would then act to continually recharge injector 10 device to compensate for any gas leakage during storage due to gas permeability. The amount of $CO_2$ will depend upon a number of factors including the size of gas spring 66, the viscosity of the medicament, the intended delivery site (e.g. subcutaneous, intramuscular, etc.), etc. For a chamber having a volume of approximately 2.5 cc, about 1 gram of solid $CO_2$ would be sufficient to jet inject most medicament subcutaneously. Threads 62 on proximal housing 40 are threaded into threads 64 to complete the assembly of power pack assembly 14.

Gas spring 66 biases ram 68 in the proximal direction. However, interference between latch 50 and recess 88 on ram 68 prevents movement of ram 68 in the proximal direction. As base member 48 and latch 50 are resilient, latch 50 could flex outward to eliminate the interference between latch 50 and recess 88, thereby allowing movement of ram 68. However, rim 92 of cap 84 blocks any flexing of latch 50. In order to remove this blockage, collar 38 must be moved distally so that rim 92 no longer interferes with outward flexing of latch 50.

As previously described, cartridge assembly 12 is inserted into proximal housing 40 and snapped into place. The insertion can be facilitated by chamfered edges 96. Additionally, forming proximal housing 40 in two sections allows some separation between the first and second sections 54, 60 to further facilitate insertion. Once cartridge assembly 12 has been inserted into power pack assembly 14, a housing retainer 98 is slid over proximal housing 40 to hinder removal of cartridge assembly 12. One important safety aspect of retainer 98 is that cartridge assembly 12 cannot become a dangerous projectile when injector 10 is fired. When cartridge assembly 12 is inserted into power pack assembly 14, the proximal end of ram 68 contacts the distal end of plunger 22 and the end of body 82 of collar 38 extends beyond the end of cartridge assembly 12.

Figure 17:
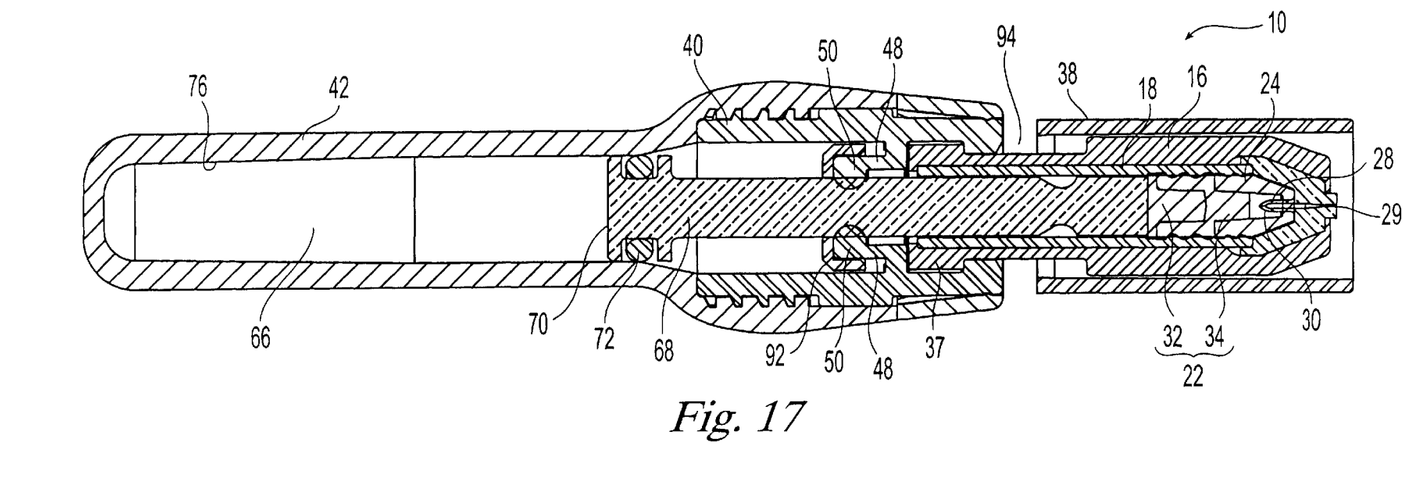
FIG. 17 shows a cross sectional view of the jet injector of FIG. 1 after firing.

The operation of injector 10 will now be described with reference to FIGS. 1 and 17. In order to fire injector 10, the proximal end of collar 38 is placed against the skin at the desired injection site. The pressure against the skin causes struts 86 to move distally in channel 90, thereby placing the end of cartridge assembly into contact with the skin. The movement of collar 38 moves rim 92 of cap 84 so that rim 92 no longer interferes with outward flexing of latch 50. The gas spring (i.e. the gas located in chamber 66) forces ram 68 and plunger 22 in the proximal direction. The movement of plunger 22 in the direction of the proximal end causes compression of the medicament. This force continues to build until stopper 24 begins to move. At that time, plunger 22, stopper 24 and the medicament, located in chamber 20, move towards the proximal end of cartridge assembly 12. This array of plunger 22, medicament, and stopper 24 moves as one unit until stopper 24 comes in contact with piercing end 30 of needle 28. Piercing end 30 of needle 28 pierces stopper 24 to create a fluid pathway for the medicament. Stopper 24 ceases to move while plunger 22 continues to respond to the force exerted on it and moves toward the proximal end of cartridge assembly 12 until all the medicament located in chamber 20 is expelled through orifice 29 at a pressure sufficient to jet inject the medicament. As ram 68 reaches the end of its stroke, which is located near a ramped region 100 of distal housing 42, the seal created by o-ring 72 is reduced to allow $CO_2$ gas to escape. Once the gas escapes, injector 10 is completely depressurized and safe to dispose.

In an exemplary embodiment, injector 10 is a single-use disposable injector that cannot be re-used. Injector 10 can have a number of mechanisms, either alone or in combinations, to achieve this. For example, the depressurization of gas spring 66 is such that it cannot be re-pressurized by the end user. Furthermore, the housing retainer 98 hinders removal of cartridge assembly 12 from power pack assembly 14 to discourage refilling of cartridge assembly 12.

Figure 18:
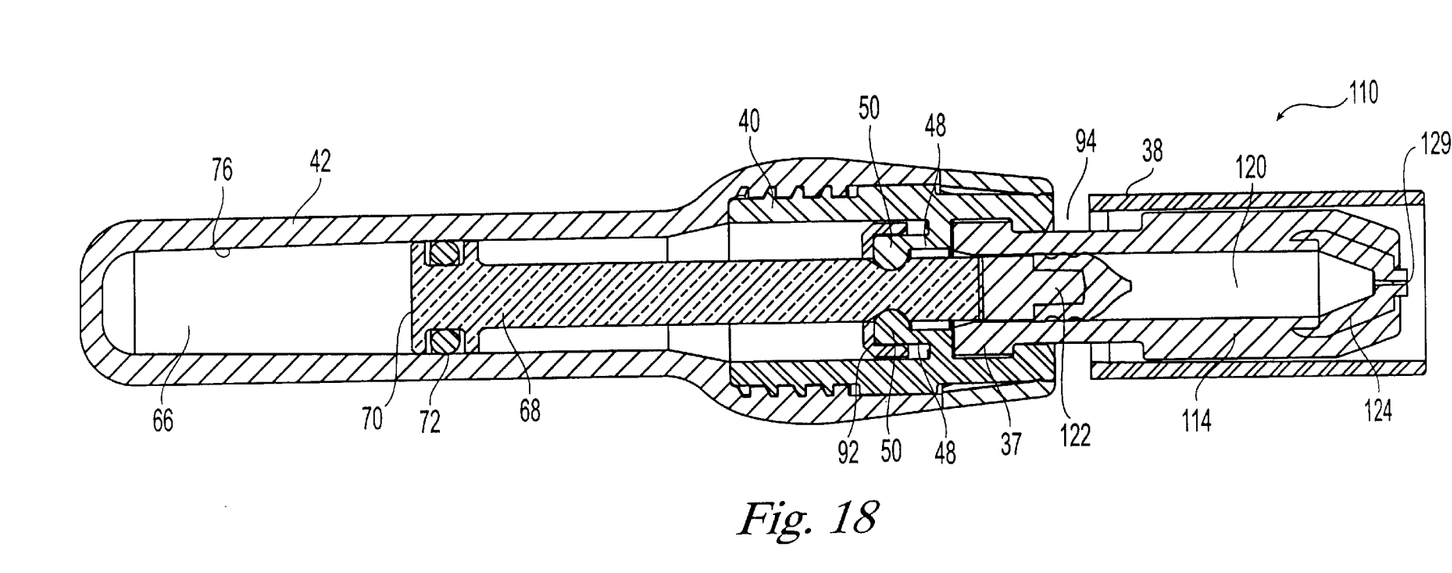
FIG. 18 shows a cross sectional view of another embodiment of the jet injector according to the present invention prior to firing.
Figure 19:
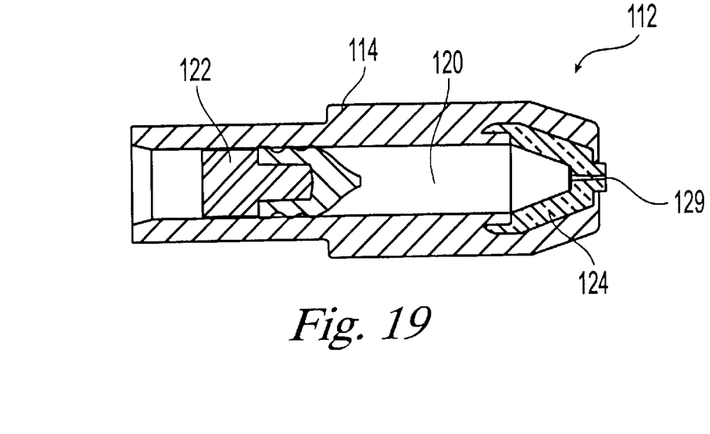
FIG. 19 shows a cross sectional view of another embodiment of a cartridge assembly.

The two assembly (cartridge and power pack) design allows an individual assembly to be modified without affecting the other assembly. For example, FIGS. 18 and 19 show another embodiment of a cartridge assembly 112 that can be used with power pack assembly 14. In general, most of the structure of cartridge assembly 112 is like or comparable to the structure of cartridge assembly 12. Accordingly, the same reference numeral is used for like components. Cartridge assembly 112 has a single housing 114 forming a chamber 120, a movable plunger 122 and a non-movable stopper 124 with an orifice 129. Although stopper 124 is shown as a discrete component attached to housing 114, housing 114 can be made to include a front end having a fluid pathway from chamber 120 to orifice 129, thereby eliminating a separate stopper.

While it is apparent that the illustrative embodiments of the invention herein disclosed fulfil the objectives stated above, it will be appreciated that numerous modifications and other embodiments may be devised by those skilled in the art. For example, the injector may be packaged ready-to-use with the cartridge and power pack assemblies connected as a functioning unit. Alternatively, the cartridge and power pack assemblies can be packaged separately and are coupled by the end user before use. In an exemplary embodiment, the injector does not have means for adjusting volume or setting the amount of volume to be injected. Rather, the injector delivers all the medicament in the device except for dead volume. As such, the volume to be injected is dependent on the volume of medicament used to fill the medicament chamber. In the embodiment of the device where it is prefilled, this depends on the fill volume. Given the numerous modifications and embodiments, it will be understood that the appended claims are intended to cover all such modifications and embodiments which come within the spirit and scope of the present invention.

What is claimed is:

1. A jet injector comprising:
    a cartridge assembly for holding medicament, the cartridge assembly having proximal and distal ends and comprising:
        a chamber having proximal and distal ends for holding the medicament therein;
        an orifice at the proximal end of the cartridge assembly;
        a stopper at the proximal end of the chamber; and
        a plunger at the distal end of the chamber and movable towards the stopper to expel medicament out of the chamber through the orifice; and
    a power pack assembly comprising:
        a housing having a proximal end operatively coupled with the distal end of the cartridge assembly;
        a trigger; and
        an energy source operatively associated with the trigger so that movement of the trigger causes the energy source to move the plunger toward the stopper to expel medicament from the chamber, wherein the energy source comprises a gas spring of a spring material in a gaseous phase and a charging portion of the spring material in a liquid phase that is in equilibrium with the gaseous phase for compensating for leakage to maintain a pressure of the gas spring prior to activation sufficient for expelling and injecting the medicament, wherein the energy source is configured for releasing the gas after the expelling of the medicament.

2. The jet injector of claim 1 further comprising a needle operatively associated with the proximal end of the cartridge assembly and having a piercing end extending toward the chamber, wherein the stopper is movable within the chamber toward the piercing end of the needle and relative movement between the stopper and the needle causes the piercing end of the needle to pierce the stopper to create a fluid pathway for the medicament through the needle and movement of the plunger toward the proximal end of the chamber compresses the medicament held between the plunger and the stopper so that the medicament is expelled through the fluid pathway.

3. The jet injector of claim 2 wherein the stopper has a frustroconical shape.

4. The jet injector of claim 3 wherein the plunger has a medicament contacting surface configured and dimensioned to mate with the frustroconical shape of the stopper to minimize volume of medicament remaining in the chamber after the injection is completed.

5. The jet injector of claim 4 wherein the stopper has a narrow cross-section where the needle penetrates the stopper.

6. The jet injector of claim 2 wherein movement of the plunger toward the proximal end of the chamber compresses the medicament between the stopper and the plunger to move the stopper toward the proximal end of the cartridge assembly to allow the piercing end of the needle to pierce the stopper and create the fluid pathway for the medicament through the needle.

7. The jet injector of claim 2 wherein the piercing end of the needle has a bevel.

8. The jet injector of claim 1 wherein the cartridge assembly comprises an outer housing made of a polymer and an inner housing made of a glass.

9. The jet injector of claim 1 wherein at least a portion of the plunger and stopper is made of an elastomeric material.

10. The jet injector of claim 1 wherein the plunger comprises a front member having a recess and an insert received in the recess, the insert being substantially non-compressible.

11. The jet injector of claim 1 wherein at least one of the plunger and stopper includes ridges formed around an outer periphery to provide a seal and create a sterile boundary between the medicament and an exterior of the cartridge assembly.

12. The jet injector of claim 1 wherein the gas spring has a wall with a coating to reduce gas permeability.

13. The jet injector of claim 1 further comprising a safety vent for releasing excess pressure.

14. The jet injector of claim 1 further comprising a temperature indicator for indicating that the jet injector has been exposed to temperatures outside of a set range.

15. A jet injector comprising:
    a cartridge assembly for holding medicament, the cartridge assembly having proximal and distal ends and comprising:
        a chamber having proximal and distal ends for holding the medicament therein;
        an orifice at the proximal end of the cartridge assembly;
        a stopper at the proximal end of the chamber;
        a plunger at the distal end of the chamber and movable towards the stopper to expel medicament out of the chamber through the orifice;
        locking tabs disposed at the distal end of the cartridge assembly; and
    a power pack assembly comprising:
        a trigger;
        an energy source comprising a gas spring comprising a material in a gaseous phase operatively associated with the trigger so that movement of the trigger activates the energy source to move the plunger toward the stopper to expel medicament from the chamber; and
        a housing having a proximal end operatively coupled with the distal end of the cartridge assembly, the power pack assembly housing including:

a distal housing having a lumen containing the material; and a proximal housing connectable with the distal housing and having an inner surface with a ledge for receiving the locking tabs to couple the cartridge assembly thereto.

16. The jet injector of claim 15 further comprising a ram having proximal and distal ends, the proximal end contacting the plunger and the distal end having a seal, wherein the gas spring is defined by the lumen wall and the seal.

17. The jet injector of claim 16 wherein the ram has a recess and the inner surface of the proximal housing has a latch member insertable into the recess to thereby prevent the gas spring from moving the ram and the plunger toward the stopper and wherein movement of the trigger allows the latch member to bend away from the recess to thereby allow the gas spring to move the ram and the plunger toward the stopper.

18. The jet injector of claim 17 wherein the trigger comprises a tubular body substantially covering the cartridge assembly, a cap operatively associated with the proximal housing, and struts connecting the body and the cap.

19. The jet injector of claim 16 wherein the spring material is carbon dioxide.

20. The jet injector of claim 15 wherein a portion of an exterior surface of the proximal housing has threads and a portion of a lumen wall has threads, the proximal housing threads mating with the lumen wall threads to connect the proximal and distal housings.

21. The jet injector of claim 15, wherein the gas spring comprises a liquid phase in equilibrium with the gaseous phase to maintain a pressure of the gaseous phase prior to activation.

22. A jet injector comprising:

a cartridge assembly for holding medicament, the cartridge assembly having proximal and distal ends and comprising:
　a chamber for holding the medicament therein and having proximal and distal ends with an orifice at the proximal end for passage of the medicament therethrough; and
　a plunger at the distal end of the chamber and movable towards the orifice to expel medicament out of the chamber through the orifice; and a power pack assembly comprising:
　a housing having a proximal end operatively coupled with the distal end of the cartridge assembly;
　a trigger; and
　an energy source operatively associated with the trigger so that movement of the trigger causes the energy source to move the plunger toward the orifice to expel medicament from the chamber, wherein the energy source comprises a gas spring of a spring material in a gaseous phase and a charging portion of the spring material in a liquid phase that is in equilibrium with the gaseous phase for compensating for leakage to maintain a pressure of the gas spring, prior to the movement of the trigger, sufficient for expelling and injecting the medicament, wherein the energy source is configured for releasing the gas after the expelling of the medicament.

23. The jet injector of claim 22, further comprising a ram that is biased by the gas spring towards the plunger for expelling the medicament when the trigger is moved, wherein the ram comprises a seal that is sealingly associated with the gas spring to seal the gas therein, the energy source and seal being configured for allowing the gas to escape after the expelling of the medicament.

24. The jet injector of claim 23, further comprising a latch member preventing movement of the ram to move the plunger, wherein the trigger is operably associated with the latch member for causing the latch member to release the ram to permit the movement of the ram against the plunger.

25. The jet injector of claim 22, further comprising a temperature sensor configured for disabling the injector to prevent the expelling of the medicament.

26. The jet injector of claim 22, wherein the energy source is configured for substantially completely depressurizing the gas after the expelling of the medicament.

27. The jet injector of claim 22, wherein the energy source is configured for releasing the gas after the expelling of the medicament to substantially prevent repressurization by a user.

28. The jet injector of claim 22, further comprising a ram that is biased prior to the movement of the trigger by the energy source towards the plunger for expelling the medicament when the trigger is moved.

29. A jet injector comprising:

a cartridge assembly for holding medicament, the cartridge assembly having proximal and distal ends and comprising:
　a chamber for holding the medicament therein and having proximal and distal ends with an orifice at the proximal end for passage of the medicament therethrough; and
　a plunger at the distal end of the chamber and movable towards the orifice to expel medicament out of the chamber through the orifice; and a power pack assembly comprising:
　a housing having a proximal end operatively coupled with the distal end of the cartridge assembly;
　a trigger;
　a ram configured and disposed for moving the plunger to expel the medicament; and
　an energy source comprising a gas spring containing gas associated with the trigger so that movement of the trigger causes the energy source to move the ram towards the plunger to expel the medicament from the chamber, wherein the gas spring biases the ram towards the plunger prior to the movement of the trigger, and the energy source is configured for releasing the gas after the expelling of the medicament.

30. The jet injector of claim 29, further comprising a latch member preventing movement of the ram to move the plunger, wherein the trigger is operably associated with the latch member for causing the latch member to release the ram to permit the movement of the ram against the plunger.

31. The jet injector of claim 29, wherein the energy source is configured for releasing the gas after the expelling of the medicament.

32. The jet injector of claim 29, wherein the gas is of a spring material in a gaseous phase, and the gas spring comprises a charging portion of the spring material in a liquid phase that is in equilibrium with the gaseous phase for compensating for leakage to maintain a pressure of the gas spring, prior to the movement of the trigger, sufficient for expelling and injecting the medicament.

* * * * *

UNITED STATES PATENT AND TRADEMARK OFFICE
CERTIFICATE OF CORRECTION

PATENT NO. : 6,682,504 B2
DATED : January 27, 2004
INVENTOR(S) : Nelson

It is certified that error appears in the above-identified patent and that said Letters Patent is hereby corrected as shown below:

Title page,
Item [*] Notice, "309 days" should read -- 0 days --.

Signed and Sealed this

Twenty-fourth Day of January, 2006

JON W. DUDAS
*Director of the United States Patent and Trademark Office*